United States Patent
Luo

(10) Patent No.: US 10,242,597 B2
(45) Date of Patent: Mar. 26, 2019

(54) APPARATUS FOR MOVING VEHICLE CRASH TEST DUMMY AND DUMMY TESTING APPARATUS

(71) Applicant: Baidu Online Network Technology (Beijing) Co., Ltd., Beijing (CN)

(72) Inventor: Min Luo, Beijing (CN)

(73) Assignee: Baidu Online Network Technology (Beijing) Co., Ltd., Beijing (CN)

( * ) Notice: Subject to any disclaimer, the term of this patent is extended or adjusted under 35 U.S.C. 154(b) by 96 days.

(21) Appl. No.: 15/425,108

(22) Filed: Feb. 6, 2017

(65) Prior Publication Data

US 2018/0090031 A1  Mar. 29, 2018

(30) Foreign Application Priority Data

Sep. 29, 2016 (CN) .......................... 2016 1 0865901

(51) Int. Cl.
| | |
|---|---|
| *G01M 17/007* | (2006.01) |
| *G09B 23/30* | (2006.01) |
| *G01M 99/00* | (2011.01) |
| *G01N 1/00* | (2006.01) |

(52) U.S. Cl.
CPC ......... *G09B 23/30* (2013.01); *G01M 17/0078* (2013.01); *G01M 99/007* (2013.01); *G01N 1/00* (2013.01)

(58) Field of Classification Search
CPC .. G01M 7/08; G01M 17/007; G01M 17/0078; G01M 99/007; G01N 1/00; G09B 23/30
See application file for complete search history.

(56) References Cited

U.S. PATENT DOCUMENTS

| | | | | |
|---|---|---|---|---|
| 3,939,691 A | * | 2/1976 | Stanev ....................... | B01J 3/04 73/12.01 |
| 4,084,505 A | * | 4/1978 | Ichinose ................. | B41F 15/10 101/115 |
| 4,317,353 A | * | 3/1982 | Geppelt ................. | B21D 15/04 72/18.9 |

(Continued)

FOREIGN PATENT DOCUMENTS

| | | | | |
|---|---|---|---|---|
| CN | 201385947 | | 1/2010 | |
| DE | 19802590 A1 | * | 8/1999 | ........ G01M 17/0078 |

(Continued)

*Primary Examiner* — David A Rogers
(74) *Attorney, Agent, or Firm* — Knobbe Martens Olson & Bear LLP

(57) ABSTRACT

In some embodiments, an apparatus includes: a motor disposed at an end of a dummy moving path with a shaft being parallel to the ground; a bevel gear with a driving gear and a driven gear which mesh each other, motive power being input from the shaft to the driving gear; a synchronous belt comprising at least two belt wheels and an endless belt, one belt wheel including a shaft perpendicular to the ground and obtaining a motive power input from the driven gear, the other belt wheel being disposed at the other end of the dummy moving path, and belt teeth on an inner circumferential surface of the endless belt respectively meshing with teeth grooves on an outer circumferential surface of said at least two belt wheels; a movable platform connected to a tight side of the endless belt, a dummy being connected on a surface of the platform.

11 Claims, 4 Drawing Sheets

(56) References Cited

U.S. PATENT DOCUMENTS

| | | | | |
|---|---|---|---|---|
| 5,245,856 A * | 9/1993 | Pazzaglia | G01N 19/02 | |
| | | | 73/9 | |
| 5,736,630 A * | 4/1998 | Welner | G01N 19/02 | |
| | | | 73/9 | |
| 6,023,984 A * | 2/2000 | Mazur | G01M 17/0078 | |
| | | | 73/865.3 | |
| 6,266,844 B1 * | 7/2001 | Conflitti | B60S 1/20 | |
| | | | 15/250.25 | |
| 6,422,058 B1 * | 7/2002 | Myles | G01M 17/0078 | |
| | | | 73/12.04 | |
| 6,461,295 B2 * | 10/2002 | Takada | A61B 1/121 | |
| | | | 600/114 | |
| 6,997,036 B2 * | 2/2006 | Kojima | G01M 17/0078 | |
| | | | 73/12.09 | |
| 2004/0168503 A1 * | 9/2004 | Kojima | G01M 17/0078 | |
| | | | 73/12.01 | |
| 2005/0155441 A1 * | 7/2005 | Nagata | G01M 17/0078 | |
| | | | 73/865.3 | |
| 2006/0278026 A1 * | 12/2006 | Friedman | G01M 17/007 | |
| | | | 73/865.6 | |
| 2009/0293586 A1 * | 12/2009 | Schleif | G01N 19/02 | |
| | | | 73/9 | |
| 2010/0170330 A1 * | 7/2010 | Scheepers | G01M 17/0072 | |
| | | | 73/116.01 | |
| 2011/0256969 A1 * | 10/2011 | Frankowski | F16H 7/1218 | |
| | | | 474/101 | |
| 2012/0204630 A1 * | 8/2012 | Wallich | G01M 17/0078 | |
| | | | 73/118.01 | |
| 2013/0055515 A1 * | 3/2013 | Diamond | A46B 9/04 | |
| | | | 15/28 | |
| 2014/0014473 A1 * | 1/2014 | Zecha | G01M 17/0078 | |
| | | | 198/617 | |
| 2014/0080647 A1 * | 3/2014 | Sakamoto | F16G 1/10 | |
| | | | 474/205 | |
| 2014/0283579 A1 * | 9/2014 | Covic | G01M 17/0078 | |
| | | | 73/12.01 | |
| 2015/0210129 A1 * | 7/2015 | Schulte | B60D 1/182 | |
| | | | 280/480 | |
| 2016/0054199 A1 | 2/2016 | Fritz et al. | | |
| 2016/0153866 A1 * | 6/2016 | Straeten | G01M 17/0078 | |
| | | | 73/12.04 | |

FOREIGN PATENT DOCUMENTS

| | | | | |
|---|---|---|---|---|
| DE | 102008030208 A1 * | 12/2009 | | G01M 17/0078 |
| DE | 102008030208 A1 * | 12/2009 | | G01M 17/0078 |
| DE | 102011017146 A1 * | 10/2012 | | G01M 17/0078 |
| DE | 102008030208 B4 * | 12/2012 | | G01M 17/0078 |
| DE | 102013214936 A1 * | 9/2014 | | G01M 17/0078 |
| WO | WO-2014147253 A2 * | 9/2014 | | G01M 17/0078 |

* cited by examiner

APPARATUS FOR MOVING VEHICLE CRASH TEST DUMMY AND DUMMY TESTING APPARATUS

CROSS-REFERENCE TO RELATED APPLICATIONS

This application claims the benefit of Chinese Patent Application No. 201610865901.6, entitled "Apparatus for Moving Vehicle Crash Test Dummy and Dummy Testing Apparatus," filed on Sep. 29, 2016, which is incorporated by reference in its entirety.

TECHNICAL FIELD

The present disclosure relates to the field of vehicle test, and specifically to the field of vehicle crash test, and more specifically to an apparatus for moving a dummy for vehicle crash test and a dummy testing apparatus.

BACKGROUND

As vehicle technologies develop, there are increasing demands for testing extremity situations of vehicles. Vehicle testing scenarios need to include experiments for testing potential impacts, but it is very dangerous to complete crash test with a real person and impossible to ensure safety of the testee.

At present, it is usual to use a gantry and guide rails fixed on the ground to move a dummy in China and abroad and thereby use the dummy to complete the vehicle crash test. However, as for the apparatus using the dummy to complete vehicle crash test, fixing guide rails on the ground causes damage to the ground, and it is very difficult to implement transport of the dummy testing apparatus.

SUMMARY

An object of some embodiments of the present disclosure is to provide an improved apparatus for moving a vehicle crash test dummy and a dummy testing apparatus to solve the technical problem as raised in the above BACKGROUND.

In a first aspect, some embodiments of the present disclosure provide an apparatus for moving a vehicle crash test dummy, the moving apparatus comprising: a motor disposed at an end of a dummy moving path, with a shaft of the motor being parallel to the ground; a bevel gear comprising a driving gear and a driven gear which mesh each other, motive power being input from the shaft of the motor to the driving gear; a synchronous belt comprising at least two belt wheels and an endless belt, one of the at least two belt wheels including a shaft perpendicular to the ground and obtaining a motive power input from the driven gear, other belt wheels of the at least two belt wheels being disposed at the other end of the dummy moving path, and belt teeth on an inner circumferential surface of the endless belt respectively meshing with teeth grooves on an outer circumferential surface of said at least two belt wheels; a movable platform connected to a tight side of the endless belt, a dummy being connected on a surface of the movable platform.

In some embodiments, the moving apparatus further comprises a reduction gearbox with an input shaft being connected to the shaft of the motor, and an output shaft being connected to the driving gear.

In some embodiments, the moving apparatus further comprises: a photoelectric sensor disposed at at least one end of the dummy moving path, connected to a control circuit board, and used to convert a detected light signal into an electrical signal and send it to the control circuit board; the control circuit board receives the electrical signal and, in response to the electrical signal being smaller than a predetermined threshold, sends a reverse rotation signal to a controller of the motor to control the motor to rotate reversely.

In some embodiments, the synchronous belt further comprises a tensioning wheel; and/or said other belt wheels comprise: a plurality of belt wheels arranged in a linear or curved form in a predetermined transmission direction of the synchronous belt.

In some embodiments, an inner circumferential surface of a loose side of the endless belt surrounds an outer circumferential surface of one of the tensioning wheels to allow a portion of the endless belt adjacent to the driven gear to be lower or higher than a portion of the endless belt away from the driven gear.

In some embodiments, a bottom of the movable platform is provided with a roller rolling along the ground; and/or two lateral sides of the movable platform parallel to the dummy moving path extend downward into a bent edge or an arc edge.

In some embodiments, the moving apparatus further comprises: a driving force boxdriving force box including the motor and one of the belt wheels disposed therein; and/or a driven counterweight box including the other of the belt wheels disposed therein.

In some embodiments, the driving force box includes a support frame, the support frame supporting a motor casing of the motor and a bearing of the driven wheel.

In some embodiments, the support frame includes a support and/or a counterweight.

In some embodiments, the driven counterweight box includes a box cover and/or a counterweight.

In some embodiments, the moving apparatus further comprises a hand wheel or handle mounted coaxially with the driven gear.

In a second aspect, some embodiments of the present disclosure provide a dummy testing apparatus for vehicle crash test, the dummy testing apparatus comprising the above moving apparatus; and a dummy connected to a surface of the movable platform of the moving apparatus.

In the apparatus for moving a vehicle crash test dummy and the dummy testing apparatus according to some embodiments of the present disclosure, the motor is disposed at an end of a dummy moving path, and includes a shaft being parallel to the ground. The bevel gear is provided and comprises a driving gear and a driven gear which mesh each other, motive power being input from the shaft of the motor to the driving gear; the synchronous belt is provided and comprises a belt wheel, a tensioning wheel and an endless belt; the belt wheel includes a shaft perpendicular to the ground and obtains a motive power input from the driven gear, the tensioning wheel is disposed at the other end of the dummy moving path, and belt teeth on an inner circumferential surface of the endless belt respectively mesh with teeth grooves on an outer circumferential surface of the belt wheel and the tensioning wheel; meanwhile, the movable platform is provided and connected to the tight side of the endless belt, and a dummy is connected on the surface of the platform. In this way, the apparatus for moving a vehicle crash test dummy and the dummy testing apparatus according to some embodiments of the present disclosure achieves modularized design of the moving apparatus, needn't destroy the ground and facilitates movement and installation of the moving apparatus and the dummy testing apparatus.

BRIEF DESCRIPTION OF THE DRAWINGS

Other features, objectives and advantages of the present disclosure will be made more apparent by reading through detailed description of unrestrictive embodiments with reference to the following figures.

FIG. 2b is a side view of the moving apparatus in FIG. 2a;

FIG. 2c is a side view of a driving force box in FIG. 2a;

FIG. 2d is a side view of a driven counterweight box in FIG. 2a; and

DETAILED DESCRIPTION OF EMBODIMENTS

The present application will be further described below in detail in combination with the accompanying drawings. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that the embodiments in the present application and the features in the embodiments may be combined with each other on a non-conflict basis. The present application will be described below in detail with reference to the accompanying drawings.

Figure 1:
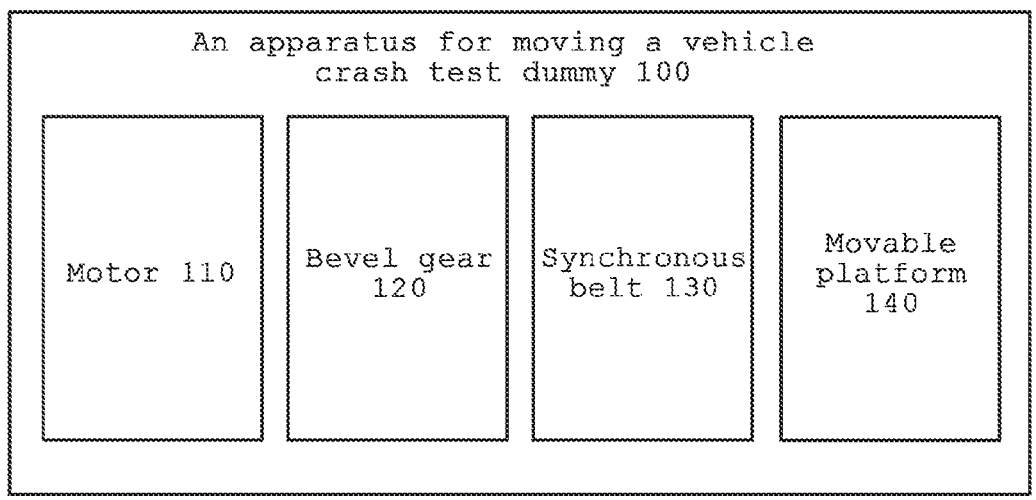
FIG. 1 is a block diagram of an apparatus for moving a vehicle crash test dummy according to some embodiments of the present disclosure.

Referring to FIG. 1, FIG. 1 is a block diagram of an apparatus for moving a vehicle crash test dummy according to some embodiments of the present disclosure.

Exemplarily, as shown in FIG. 1, the apparatus 100 for moving a vehicle crash test dummy may comprise but is not limited to: a motor 110, a bevel gear 120, a synchronous belt 130 and a movable platform 140.

Wherein, the motor 110 is disposed at an end of a dummy moving path, with a shaft of the motor being parallel to the ground; the bevel gear 120 comprises a driving gear and a driven gear which mesh each other, motive power being input from the shaft of the motor to the driving gear; the synchronous belt 130 comprises at least two belt wheels and an endless belt, one of the at least two belt wheels includes a shaft perpendicular to the ground and obtains a motive power input from the driven gear, other belt wheels of the at least two belt wheels are disposed at the other end of the dummy moving path, and belt teeth on an inner circumferential surface of the endless belt respectively mesh with teeth grooves on an outer circumferential surface of said at least two belt wheels; the movable platform 140 is connected to a tight side of the endless belt, and a dummy is connected on the surface of the platform.

In some embodiments of the present disclosure, the motor 110 is used to provide motive power to the moving apparatus 100. It is feasible to determine a rated power and a rated rotation speed of the motor according to a weight of the dummy to be moved, a movement speed to be achieved by the dummy, and a transmission loss between the motor and the dummy. Since a lower rotation speed is needed in some embodiments of the present disclosure, a low-speed motor may be employed for implementation. For example, low-speed driving is implemented by using a gear head motor, an electromagnetic deceleration motor, a torque motor, a claw pole synchronous motor or the like.

The bevel gear 120 comprises a driving gear and a driven gear and used to achieve transmission between two intersecting shafts, an intersection angle of the two shafts is called a shaft angle, and its value may be determined according to transmission needs, generally 90°. Gear teeth are arranged on a truncated cone, and gear teeth gradually taper and become smaller from a large end to a small end of the gear. Teeth of the bevel gear are in a form of straight teeth, slant teeth and curved teeth. In some embodiments of the present disclosure, since the transmission speed is lower, a straight-tooth or slant-tooth bevel gear which is simpler in design, manufacture and installation may be employed. A transmission ratio of the driving gear to the driven teeth may be determined based on the rotation speed of the motor and the movement speed of the dummy.

The synchronous belt 130 is an endless belt with a steel wire rope or glass fiber as a strength layer, cladded with polyurethane or neoprene. The inner circumference of the belt is formed with teeth which mesh with toothed belt wheel. Upon driving the synchronous belt to transmit, the toothed belt wheel includes an accurate transmission rate, includes a small acting force to the shaft, is structurally impact, resistant against oil, wear and aging, is generally used at a temperature in a range of −20° C.-80° C., at a speed v<50 m/s, a power P<300 kw and a transmission ratio i<10, and may be used for low-speed transmission. The number of belt wheels may be set as two or more according to actual needs, and one of the belt wheels is set as a power input wheel.

The movable platform 140 may be made of various materials resistant against impact and pressure, and a connection manner and positional relationship of the movable platform and the synchronous belt may be a connection manner and positional relationship in the prior art or in technologies to be developed in the future, and this is not limited in the present disclosure. For example, the movable platform may be connected to an upper surface of the tight side of the endless belt, or connected to a lower surface of the tight side of the endless belt, or the tight side may be arranged through the movable platform. For example, the platform may be made of a stainless steel. The shape of the movable platform may be a plate shape provided with a special structure.

In some optional implementation modes of some embodiments of the present disclosure, for example, the above motor is an ordinary motor. To lower the rotation speed of the motor, a decelerator may be mounted between the motor and the driving gear, that is to say, the moving apparatus further comprises a reduction gearbox (not shown in FIG. 1) with an input shaft being connected to the shaft of the motor, and an output shaft being connected to the driving gear.

In some optional implementation modes of some embodiments of the present disclosure, when the dummy moves to an end of the moving path, it needs to automatically return along the moving path. Hence, the moving apparatus may be arranged to further comprise: a photoelectric sensor (not shown in FIG. 1) disposed at at least one end of the dummy moving path, connected to a motor control circuit board, and used to convert the detected light signal into an electrical signal and send it to the motor control circuit board; the control circuit board (not shown in FIG. 1) receives the electrical signal and, in response to the electrical signal being smaller than a predetermined threshold, sends a reverse rotation signal to a controller of the motor to control the motor to rotate reversely.

Here, the number of the photoelectrical sensor may be one or more, and the photoelectrical sensor may be disposed at one end or both ends of the moving path according to movement needs of the dummy.

In some optional implementation modes of some embodiments of the present disclosure, the synchronous belt further comprises a tensioning wheel (not shown in FIG. 1); and/or other belt wheels (not shown in FIG. 1) comprise: a plurality of belt wheels arranged in a linear or curved form in a predetermined transmission direction of the synchronous belt.

In the present implementation mode of some embodiments of the present disclosure, to further tension the synchronous belt, one or more tensioning wheels may be disposed on the basis of at least two belt wheels. The tensioning wheels generally should be disposed inside of the loose side to allow the belt to be only subjected to single-side curving. Meanwhile, the tensioning wheels should try to approach the large wheel to avoid excessively affecting a wrap angle on the small belt wheel. Wheel grooves of the tensioning wheels are dimensioned identical with the belt wheels.

In some optional implementation modes of some embodiments of the present disclosure, the inner circumferential surface of the loose side of the endless belt surrounds the outer circumferential surface of one tensioning wheel to allow a portion of the endless belt adjacent to the driven gear to be lower than or higher than a portion of the endless belt (not shown in FIG. 1) away from the driven gear.

In the present implementation mode of some embodiments of the present disclosure, the loose side of the synchronous belt is arranged to surround the outer circumferential surface of the tensioning wheels so that there is a height difference between the height of the loose side and the height of the tight side, thereby avoiding friction of the loose side and the movable platform connected on the tight side, and thereby reducing transmission loss and improving a transmission efficiency.

In some optional implementation modes of some embodiments of the present disclosure, a bottom of the movable platform is provided with a roller (not shown in FIG. 1) rolling along the ground; and/or two lateral sides of the movable platform parallel to the dummy moving path extend downward into a bent edge or an arc edge (not shown in FIG. 1).

In the present implementation mode of some embodiments of the present disclosure, providing the roller on the bottom of the movable platform may improve a balancing capability of the movable platform and reduce a probability of turnover of the movable platform while being pulled. Hence, when rollers are provided, they may be disposed in proximity with the lateral side of the movable platform and arranged symmetrically to further improve the balance of the movable platform. Since the movable platform is used to connect the dummy, a portion of the rollers may be embedded in the movable platform to reduce a distance of a top surface of the movable platform from the ground. Alternatively or additionally, since the dummy might roll over the platform upon vehicle crash test, a bent edge or an arcuate edge may be disposed on both sides of the movable platform so that the dummy in the crash test may smoothly roll over the movable platform.

In some optional implementation modes of some embodiments of the present disclosure, the moving apparatus further comprises: a driving force box (not shown in FIG. 1) in which the motor and one of the belt wheels are disposed; and/or a driven counterweight box (not shown in FIG. 1) in which said other belt wheels are disposed.

In the present implementation mode of some embodiments of the present disclosure, to protect the motor and belt wheel, the driving force box may be disposed to arrange the motor and one of said belt wheels; alternatively or additionally, the driven counterweight box may be disposed to protect said other belt wheels.

In some optional implementation modes of some embodiments of the present disclosure, in the driving force box is further provided a support frame (not shown in FIG. 1) on which are provided a motor casing of the motor and a bearing for supporting the driven wheel (not shown in FIG. 1).

In the present implementation mode of some embodiments of the present disclosure, the support frame is disposed in the driving force box to support the motor casing of the motor and the bearing of the driven wheel so that a power device of the moving apparatus operates smoothly.

In some optional implementation modes of some embodiments of the present disclosure, the support frame is provided with a support (not shown in FIG. 1) and/or a counterweight (not shown in FIG. 1).

In the present implementation mode of some embodiments of the present disclosure, the support frame is provided with a support to support the weight of the support frame and the equipment carried by it. The support is fixed at a certain position and bears vibration upon operation and earthquake load. Alternatively or additionally, the support frame is provided with the counterweight to enhance stability of the support frame.

In some optional implementation modes of some embodiments of the present disclosure, driven counterweight box is provided with a box cover (not shown in FIG. 1) and/or a counterweight (not shown in FIG. 1).

In the present implementation mode of some embodiments of the present disclosure, the box cover provided for the driven counterweight box may protect other belt wheels in the driven counterweight box; alternatively or additionally, the counterweight is provided for the driven counterweight box to enhance stability of the driven counterweight box.

In some optional implementation modes of some embodiments of the present disclosure, the moving apparatus further comprises (not shown in FIG. 1): a hand wheel or handle mounted coaxially with the driven gear.

In the present implementation mode of some embodiments of the present disclosure, with the hand wheel or handle being arranged, the synchronous belt may be manually operated to turn to thereby move the dummy and improve applicability of the moving apparatus.

It should be appreciated that the hand wheel or handle here may be a member mounted coaxially with the driven gear separately, or may also be a portion of the driven gear or said one belt wheel. The hand wheel or handle may be disposed integrally, or may be formed by connecting two or more members.

Hereunder, a specific application scenario of the apparatus for moving a vehicle crash test dummy according to some embodiments of the present disclosure will be illustrated with reference to FIG. 2a, FIG. 2b, FIG. 2c and FIG. 2d.

Figure 2A:
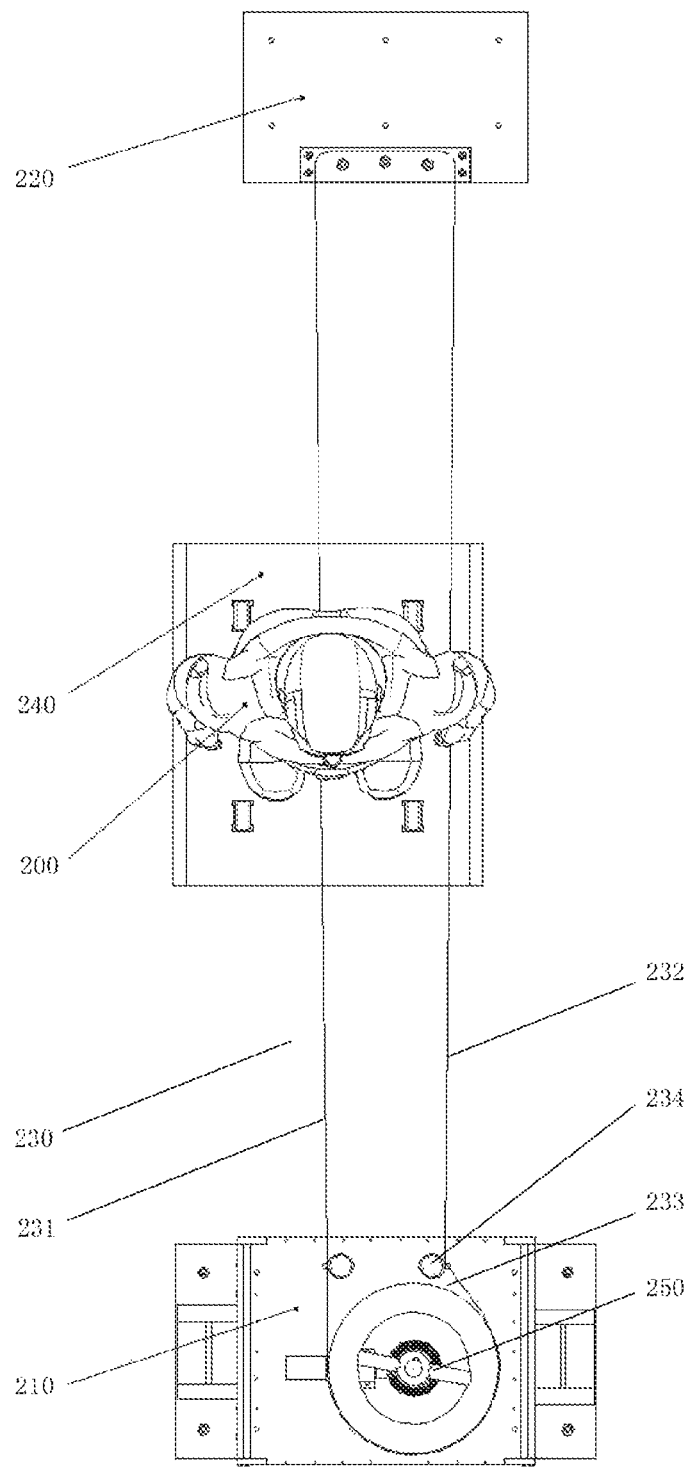
FIG. 2a is a top view of a fitting diagram of an apparatus for moving a vehicle crash test dummy according to some embodiments of the present disclosure.

FIG. 2a is a top view of a fitting diagram of an apparatus for moving a vehicle crash test dummy according to some embodiments of the present disclosure.

As shown in FIG. 2a, the moving apparatus comprises a driving force box 210, a driven counterweight box 220, a synchronous belt 230, a movable platform 240 and a hand wheel 250.

Wherein, the synchronous belt 230 comprises an endless belt which includes a tight side 231 for pulling the movable platform and a loose side 232. The synchronous belt 230 further comprises a belt wheel 233, a belt wheel 233 and a belt wheel (not shown in FIG. 2) in the driven counterweight box 220. A tensioning wheel 234 is disposed beside the belt wheel 233. The inner circumferential surface of the loose side 232 of the endless belt surrounds the outer circumferential surface of one tensioning wheel 234 to allow a portion of the endless belt adjacent to the driven gear lower than or higher than a portion of the endless belt away from the driven gear so that a height difference is formed between the tight side 231 and the loose side 232. The dummy 200 is connected on the movable platform 240 of the moving apparatus. The hand wheel 250 is used to manually turn the belt wheel to bring the dummy to move.

Figure 2B:
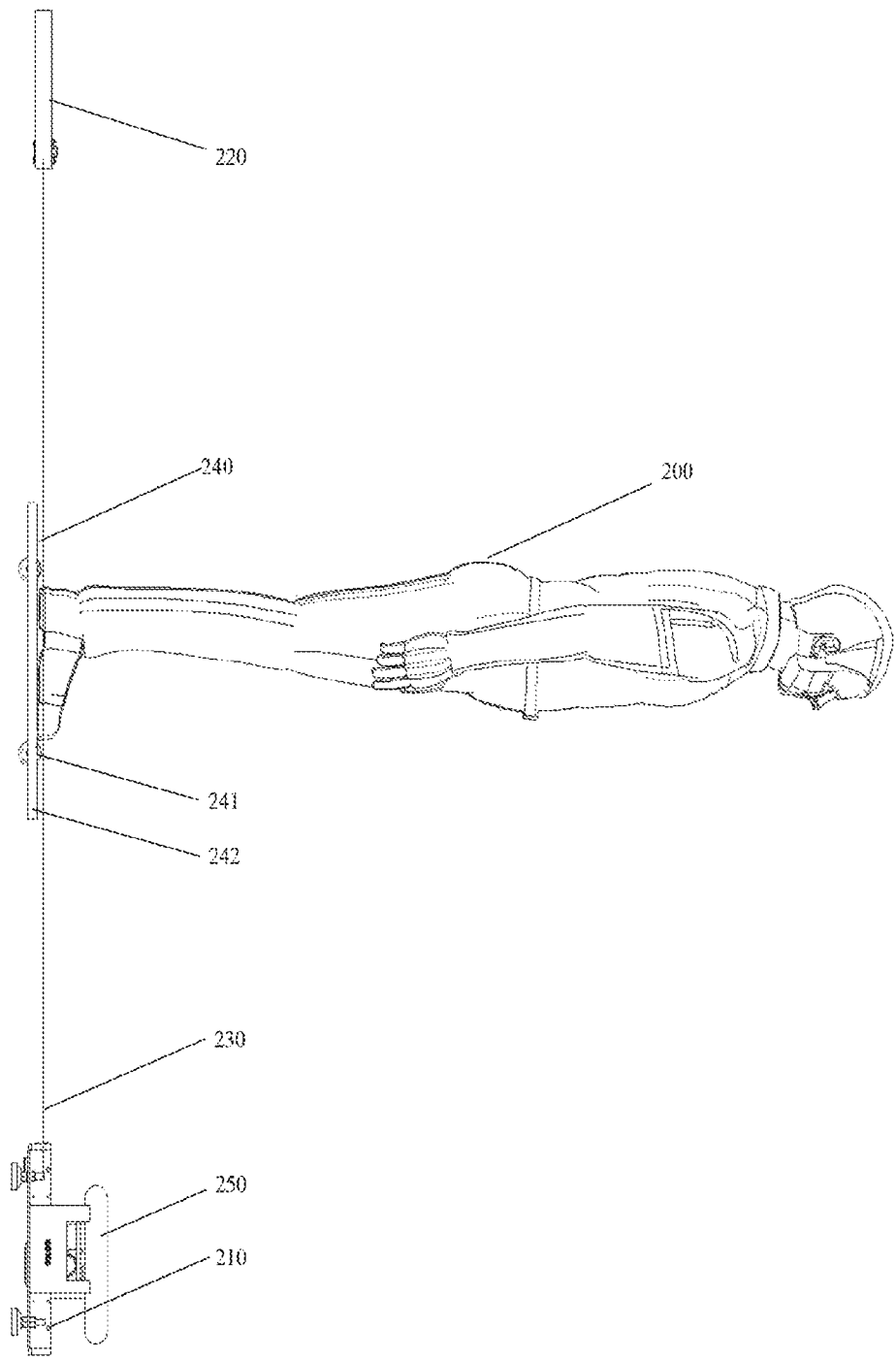

FIG. 2b is a side view of the moving apparatus in FIG. 2a.

As shown in FIG. 2b, the moving apparatus comprises the driving force box 210, the driven counterweight box 220, synchronous belt 230, movable platform 240 and hand wheel 250.

Wherein a bottom of the movable platform. 240 is provided with a roller 241 rolling along the ground, the roller 241 is embedded in the movable platform 240, and two lateral sides of the movable platform 240 parallel to the dummy moving path extend downward into a bent edge or an arc edge 242. The dummy 200 is connected on the movable platform 240 of the moving apparatus. The hand wheel 250 is used to manually turn the belt wheel to bring the dummy to move.

Figure 2C:
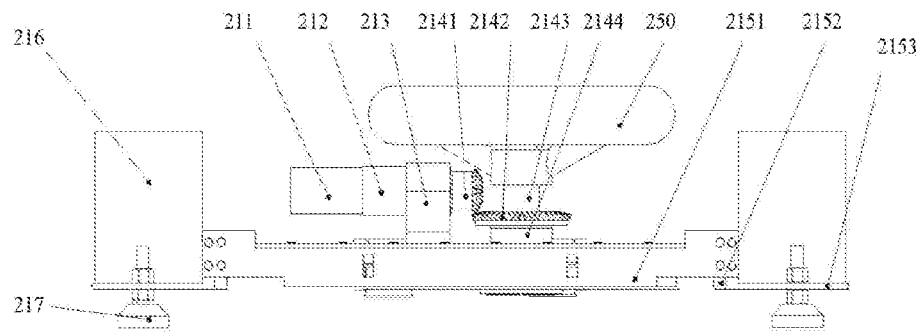

FIG. 2c is a side view of the driving force box 210 in FIG. 2a.

As shown in FIG. 2c, in the driving force box 210 are provided a motor 211, a deceleration box 212, a motor casing 213, a bevel gear (including a driving gear 2141 and a driven gear 2142), a main shaft 2143 of the driven gear 2142, a support bearing 2144 of the driven gear 2142, a hand wheel 250, a support frame (including a frame 2151, a frame 2152 and a frame 2153), a counterweight 216 disposed on the frame 2153, and a support 217 of the support frame.

Figure 2D:
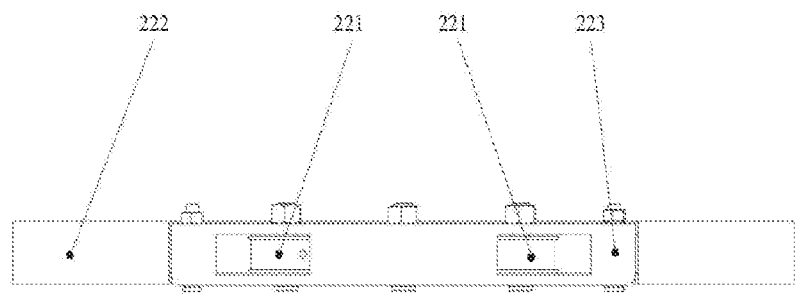

FIG. 2d is a side view of the driven counterweight box 220 in FIG. 2a.

As shown in FIG. 2d, the belt wheel 221 cooperating with the endless belt for transmission is disposed in the driven counterweight box 220, and the driven counterweight box 220 comprises a driven counterweight box body 222 and a driven counterweight box cover 223.

It should be appreciated that the structure of the apparatus for moving a vehicle crash test dummy shown in FIGS. 2a, 2b, 2c and 2d is only an illustrative structure of some embodiments of the present disclosure and does not represent a limitation to the present disclosure.

The apparatus for moving a vehicle crash test dummy according to the above embodiments of the present disclosure achieves modularized design of the moving apparatus, needn't destroy the ground and facilitates movement and installation of the moving apparatus and the dummy testing apparatus.

Figure 3:
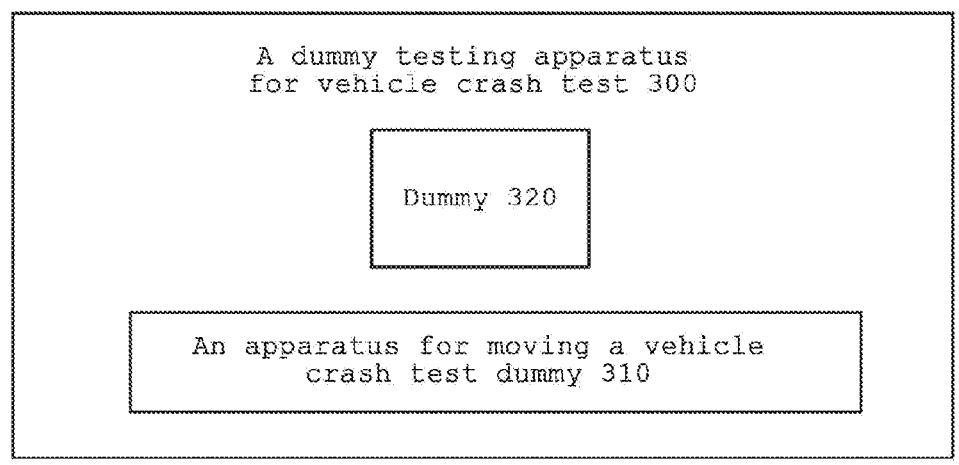
FIG. 3 is a block diagram of a dummy testing apparatus for vehicle crash test according to some embodiments of the present disclosure.

Further referring to FIG. 3, FIG. 3 is a block diagram of a dummy testing apparatus for vehicle crash test according to some embodiments of the present disclosure.

Exemplarily, as shown in FIG. 3, the dummy testing apparatus 300 for vehicle crash test may comprise an apparatus 310 for moving a vehicle crash test dummy, and a dummy 320. The dummy 320 is connected to a surface of the movable platform of the moving apparatus 310.

It should be appreciated that the apparatus 310 for moving a vehicle crash test dummy in some embodiments of the present disclosure corresponds to the above apparatus 200 for moving a dummy described with reference to FIG. 1, so the depictions of the apparatus 200 for moving a vehicle crash test dummy is also applicable for the apparatus 310 for moving a vehicle crash test dummy in the dummy testing apparatus for vehicle crash test, and will not be repeated in detail here.

The foregoing is only a description of the some embodiments of the present application and the applied technical principles. It should be appreciated by those skilled in the art that the scope of the present application is not limited to the technical solutions formed by the particular combinations of the above technical features. The scope should also cover other technical solutions formed by any combinations of the above technical features or equivalent features thereof without departing from the concept of the disclosure, such as, technical solutions formed by replacing the features as disclosed in the present application with (but not limited to), technical features with similar functions. Various components disclosed and/or illustrated in the figures may be implemented as hardware and/or software and/or firmware on a processor, ASIC/FPGA, dedicated hardware, and/or logic circuitry. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A moving apparatus for moving a vehicle crash test dummy, the apparatus comprising:
   a motor disposed at an end of a dummy moving path, the motor including a shaft of the motor parallel to a ground;
   a bevel gear comprising a driving gear and a driven gear which mesh each other, wherein motive power is configured to be inputted from the shaft of the motor to the driving gear;
   a synchronous belt comprising at least two belt wheels and an endless belt, one belt wheel of the at least two belt wheels including a shaft of the belt perpendicular to the ground and configured to obtain a motive power input from the driven gear, another belt wheel of the at least two belt wheels disposed at the other end of the dummy moving path, and belt teeth on an inner circumferential surface of the endless belt respectively meshing with teeth grooves on an outer circumferential surface of said at least two belt wheels;
   a movable platform connected to a tight side of the endless belt, a dummy configured to be connected on a surface of the movable platform; and a photoelectric sensor disposed at at least one end of the dummy moving path, connected to a control circuit board, and used to convert a detected light signal into an electrical signal and send the electrical signal to the control circuit board, wherein the control circuit board is configured to:
receive the electrical signal and, in response to the electrical signal being smaller than a predetermined threshold, send a reverse rotation signal to a controller of the motor to control the motor to rotate reversely.

2. The moving apparatus according to claim 1, further comprising:
a reduction gearbox with an input shaft connected to the shaft of the motor, and an output shaft connected to the driving gear.

3. The moving apparatus according to claim 1, wherein the synchronous belt further comprises a tensioning wheel; and/or
the another belt wheel comprises: a plurality of belt wheels arranged in a linear or curved form in a predetermined transmission direction of the synchronous belt.

4. The moving apparatus according to claim 1, wherein an inner circumferential surface of a loose side of the endless belt surrounds an outer circumferential surface of one of the tensioning wheels to allow a portion of the endless belt adjacent to the driven gear to be lower or higher than a portion of the endless belt away from the driven gear.

5. The moving apparatus according to claim 1, wherein a bottom of the movable platform is provided with a roller rolling along the ground; and/or
two lateral sides of the movable platform parallel to the dummy moving path extend downward into a bent edge or an arc edge.

6. The moving apparatus according to claim 1, further comprising:
a driving force box including the motor and one of the belt wheels disposed therein; and/or
a driven counterweight box including the other of the belt wheels disposed therein.

7. The moving apparatus according to claim 6, wherein the driving force box includes a support frame, the support frame supporting a motor casing of the motor and a bearing of the driven wheel.

8. The moving apparatus according to claim 7, wherein the support frame includes a support and/or a counterweight.

9. The moving apparatus according to claim 6, wherein the driven counterweight box includes a box cover and/or a counterweight.

10. The moving apparatus according to claim 1, further comprising a hand wheel or handle mounted coaxially with the driven gear.

11. A dummy testing apparatus for vehicle crash test, wherein the dummy testing apparatus comprises the moving apparatus according to claim 1; and
a dummy connected to a surface of the movable platform of the moving apparatus.

* * * * *